United States Patent [19]
Nordquist

[11] Patent Number: 5,754,274
[45] Date of Patent: May 19, 1998

[54] FIELD OF VISION COLLIMATOR

[75] Inventor: Robert E. Nordquist, Oklahoma City, Okla.

[73] Assignee: Wound Healing of Oklahoma, Oklahoma City, Okla.

[21] Appl. No.: 713,099

[22] Filed: Sep. 16, 1996

Related U.S. Application Data

[63] Continuation-in-part of Ser. No. 371,957, Jan. 12, 1995, Pat. No. 5,557,352.

[51] Int. Cl.⁶ .................... A61B 3/02; A61B 3/10
[52] U.S. Cl. .................... 351/223; 351/218; 351/246
[58] Field of Search .................... 351/200, 218, 351/222, 223, 233, 236, 237, 246

[56] References Cited

U.S. PATENT DOCUMENTS

| | | | |
|---|---|---|---|
| 268,016 | 11/1882 | Hardy | 351/222 |
| 484,055 | 10/1892 | Sherman | 351/222 |
| 1,510,114 | 9/1924 | Thorner | 351/237 |
| 1,747,844 | 2/1930 | Ritholz | 351/222 |
| 2,523,007 | 9/1950 | Glazer | 351/237 |
| 3,664,631 | 5/1972 | Guyton | 351/237 |
| 3,905,688 | 9/1975 | Decker et al. | 351/222 |
| 4,498,743 | 2/1985 | Feinbloom | 351/46 |
| 4,679,921 | 7/1987 | Yamada | 351/222 |
| 4,750,831 | 6/1988 | Vega | 351/223 |
| 4,875,767 | 10/1989 | Wright | 351/223 |
| 5,455,645 | 10/1995 | Berger | 351/223 |
| 5,557,352 | 9/1996 | Nordquist | 351/237 |

OTHER PUBLICATIONS

Edmund Scientific, *Off–the–Shelf Optics & Components for OEM and Research Applications*, #14N7.
Seiler Instrument, *Dioptometer*, PN 7680631.

*Primary Examiner*—Huy Mai
*Attorney, Agent, or Firm*—Fellers, Snider, Blankenship, Bailey & Tippens

[57] ABSTRACT

A field of view collimator for self-monitoring peripheral vision loss. The field of view collimator includes a hand-held housing having a viewing aperture for placement adjacent to the subject's eye. A lens projects an image to the eye. The image, in the form of a circular edge, is formed by an iris diaphragm positioned behind the lens. The angular size of the image is adjustable by opening or closing the iris diaphragm. A diffuser is positioned behind the iris diaphragm to provide an even back-illumination. Indicia markings indicate the measured field of view. The device is particularly suitable for home use by persons with glaucoma.

6 Claims, 3 Drawing Sheets

FIELD OF VISION COLLIMATOR

CROSS REFERENCE TO RELATED APPLICATION

This application is a continuation-in-part of U.S. patent application Ser. No. 08/371,957, filed Jan. 12, 1995, which application is incorporated herein by reference now U.S. Pat. No. 5,557,352.

BACKGROUND OF THE INVENTION

1. Technical Field

This invention relates generally to instruments for measuring characteristics of the human eye, and, more specifically, to a hand-held device for measuring the field of vision of an eye. The device is particularly useful for self-monitoring of persons with glaucoma.

2. Background

Glaucoma is a disease of aqueous dynamics within a closed structure, the eye. All compartments within the eye share the same watery substances, although it takes a different character in the back portion of the eye. This gel substance is called vitreous. The anterior chamber is filled with a clear, water-like fluid called aqueous. Both of these materials originate at the ciliary body. The ciliary body removes water from blood vessels and pumps the water into the eye. The rate and pressure within the normal eye is dependent on many variables but is a homeostatic system, that is, self-regulating. The normal intraocular pressure in adult humans has a range of approximately 12 to 19 mmHg.

In times of stress or hypertension, the normal eye can have an elevated pressure due to the arterial pressure increase. When dehydrated, the pressure within the eye can be significantly reduced. When the pressure inside the eye is elevated it is due to one of two factors or a combination of the two. These factors are (1) increased secretion of the ciliary body, that is, an increased amount of fluid being pumped into the eye, or (2) blockage or damage to the trabecular meshwork which is the outflow system of the eye. In some cases both of these factors are operational.

When the pressure within the eye is elevated and maintained at an elevated state, the pressure is directed backward into the optic nerve which is surrounded by a very vascular region called the cribrosa. This area is the weakest point in the wall of the eye so pressure is able to decrease the flow in the blood vascular system that supplies the optic nerve. This results in hypoxia and ultimately in the death of neurons. The most peripheral neurons suffer the greatest affects and as a result the peripheral vision becomes reduced. Normal peripheral vision has a sphere from 180° to 140°, depending on the anatomical variations of the eye.

Patients with glaucoma are followed to determine the advance of the disease by field studies that show the extent of peripheral vision loss. Normally these patients are seen at intervals of six months or one year. It would be a great advantage for the managing physician to be able to analyze this field in the patient every day.

It is thus the object of this invention to provide a device that allows the glaucoma patient to self-monitor peripheral vision loss for reporting to the managing physician.

There exist prior devices, including hand-held devices, designed to quantify refractive errors of the eye and measure visual acuity, such as those disclosed in U.S. Pat. Nos. 268,016; 484,055; 1,510,114; 1,747,844; 2,523,007; 3,664,631; 3,905,688; 4,679,921; and 5,455,645. None of the references, however, contemplates the self-measurement and reporting of peripheral vision loss by a glaucoma patient.

SUMMARY OF THE INVENTION

The present invention will enable the glaucoma patient to personally determine peripheral field loss at the earliest opportunity, allowing rapid intervention by the managing physician.

A field of view collimator allows for self-monitoring of peripheral vision loss. The field of view collimator includes a hand-held housing having a viewing aperture for placement adjacent to the subject's eye. A lens means projects an image to the eye. The image, in the form of a circular edge, is formed by an iris diaphragm positioned behind the lens means. The angular size of the image is adjustable by opening or closing the iris diaphragm. A diffuser is positioned behind the iris diaphragm to provide an even back-illumination. Indicia markings indicate the measured field of view.

The device is a home-use device particularly suitable for persons with glaucoma. At regular intervals, the subject self-tests his or her peripheral vision by holding the device first one eye, then the other (with the contralateral eye preferably covered by a patch), beginning with the iris diaphragm completely open. A knurled ring is then turned to progressively close the iris diaphragm. As soon as the circular edge of the diaphragm is visible, the subject ceases turning the knurled ring and reads the indicia markings to obtain a field of view value.

The subject records the results of the self-tests and reports the results to the managing physician, who monitors the results and intervenes with treatment as appropriate.

Still other objects and advantages of the present invention will become readily apparent to those skilled in this art from the following detailed description, wherein there is shown and described only the preferred embodiment of the invention, simply by way of illustration of the best mode contemplated for carrying out the invention. As will be realized, the invention is capable of modifications in various obvious respects, all without departing from the invention. Accordingly, the description should be regarded as illustrative in nature, and not as restrictive.

DETAILED DESCRIPTION OF THE PREFERRED EMBODIMENT

Before explaining the present invention in detail, it is to be understood that the invention is not limited in its application to the details of the construction and arrangement of parts illustrated in the accompanying drawings. The invention is capable of other embodiments and of being practiced or carried out in a variety of ways. It is to be understood that the phraseology and terminology employed herein is for the purpose of description and not of limitation.

Figure 1:
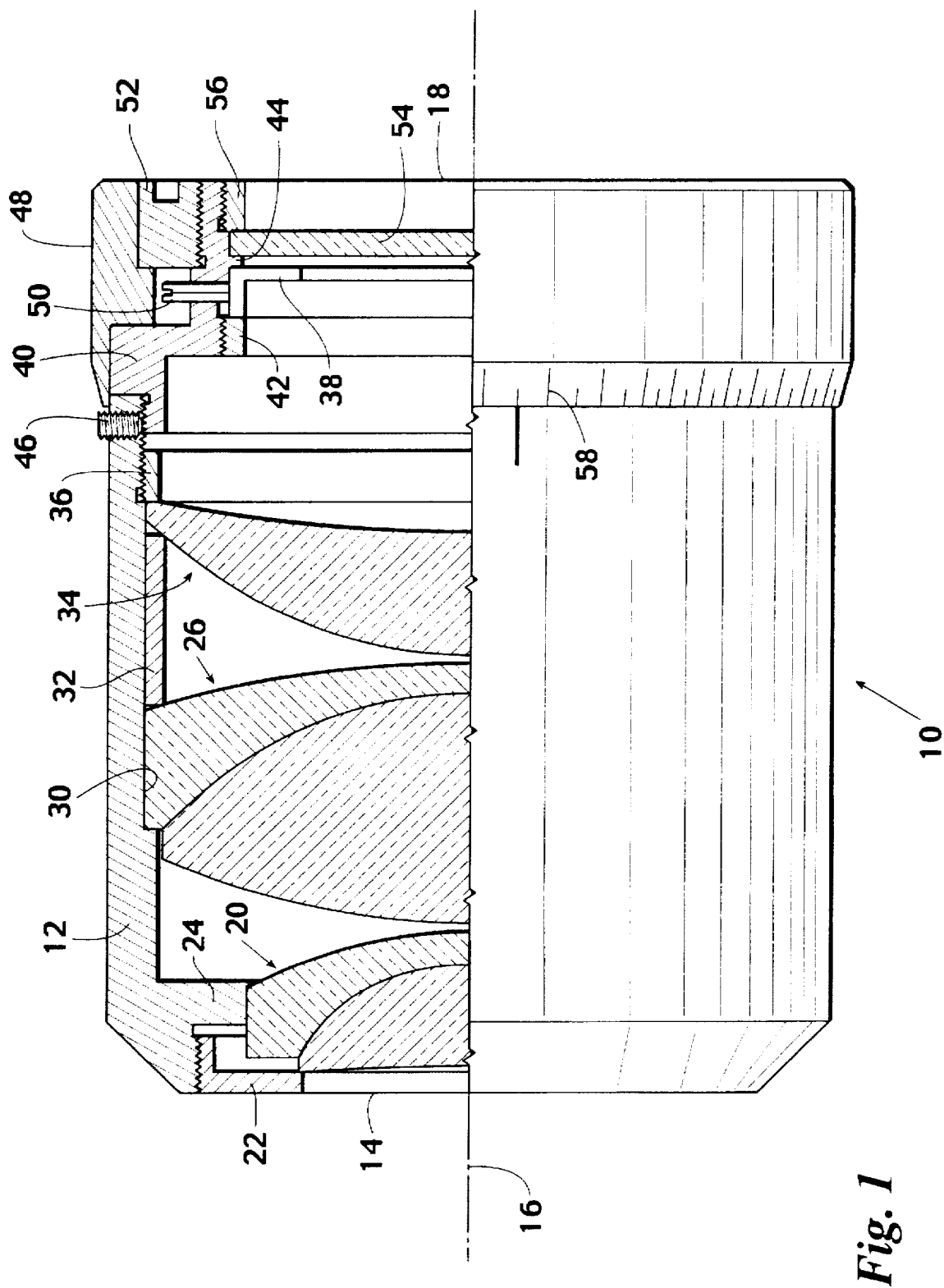
FIG. 1 is a partial cross section illustrating the preferred embodiment of the invention.

Referring first to FIG. 1, the preferred field of view collimator is generally indicated by the reference numeral 10. The collimator 10 includes a lens housing 12 having a viewing aperture 14 for placement adjacent to the eye. The viewing aperture 14 is sized to accommodate a four (4) mm diameter pupil. In use, the collimator 10 is positioned in front of the eye in a coaxial fashion along the line of sight 16. At its end opposite the viewing aperture 14, there is a terminal aperture 18. The terminal aperture 18 allows for the entry of ambient light into the interior of the collimator 10.

Near to the viewing aperture 14 is a lens complex, illustrated in the preferred embodiment as three lenses arranged in series. An initial doublet lens 20 is held in place by a first lens retainer ring 22 and an inner ledge 24 of the lens housing 12. A second doublet lens 26 is secured in a recessed area 30 of the lens housing 12. A spacer 32 separates the second doublet lens 26 from a singlet lens 34. A second lens retainer ring 36 secures the entire lens assembly. The preferred lens assembly is discussed in further detail hereinafter in relation to FIGS. 2 and 3.

The lens assembly projects an image to the eye. The image is in the form of a circular edge formed by the central opening of an iris diaphragm 38. The iris diaphragm 38 is positioned behind the lens assembly in an iris housing 40. The iris diaphragm 38 is secured between a retainer ring 42 and an inner ledge 44 of the iris housing 40. The iris housing 40 and lens housing 12 are fastened together by a set screw 46. The iris diaphragm 38 is similar in type to those used in the camera industry in connection with camera lenses. The iris diaphragm 38 can be opened or closed by turning a knurled ring 48. In a manner well known in the art, the knurled ring 48 contacts a catch-pin 50 that, when rotated, causes the circular edge defining the central opening of the iris diaphragm 38 to open or close. The preferred iris diaphragm 38 has a maximum open aperture of 60 mm and possesses the capability of full closure. The iris housing 40 and knurled ring 48 are secured in the assembly by a main retainer ring 52.

A diffuser 54, preferably made of ground glass, is positioned behind the iris diaphragm 38 and immediately in front of the terminal aperture 18. It is sandwiched between the inner ledge 44 of the iris housing 40 and a diffuser retainer ring 56. The diffuser 54 provides an even back-illumination that makes it easier for the user to focus on infinity, allowing for relaxed accommodation during the measurement exercise. Relaxed accommodation is essential, and the ground glass helps achieve this by blocking external distractions.

Indicia markings 58 correspond to the position of the central opening of the iris diaphragm 38. The indicia markings 58 indicate the measured field of view to the user.

The device is compact, easy to handle, and is particularly suited for home self testing by persons with glaucoma. With respect to its overall dimensions, the device is approximately 80 mm in diameter and 100 mm in length. The preferred half field of vision is 60°. Thus, the indicia markings 58 are calibrated in order to indicate an angular field of view from 120° down. At regular intervals, preferably daily, the subject self tests his or her peripheral vision by holding the collimator 10 first to one eye, then the other, beginning with the iris diaphragm 38 completely open. Preferably, the subject has a patch over the contralateral eye. If a patch is not available, the contralateral eye should remain open. The knurled ring 48 is then turned to progressively close the central opening of the iris diaphragm 38. As soon as the circular edge of the diaphragm 38 is visible, the subject ceases to turn the knurled ring 48 and reads the indicia markings 58 to obtain a field of view value.

Figure 2:
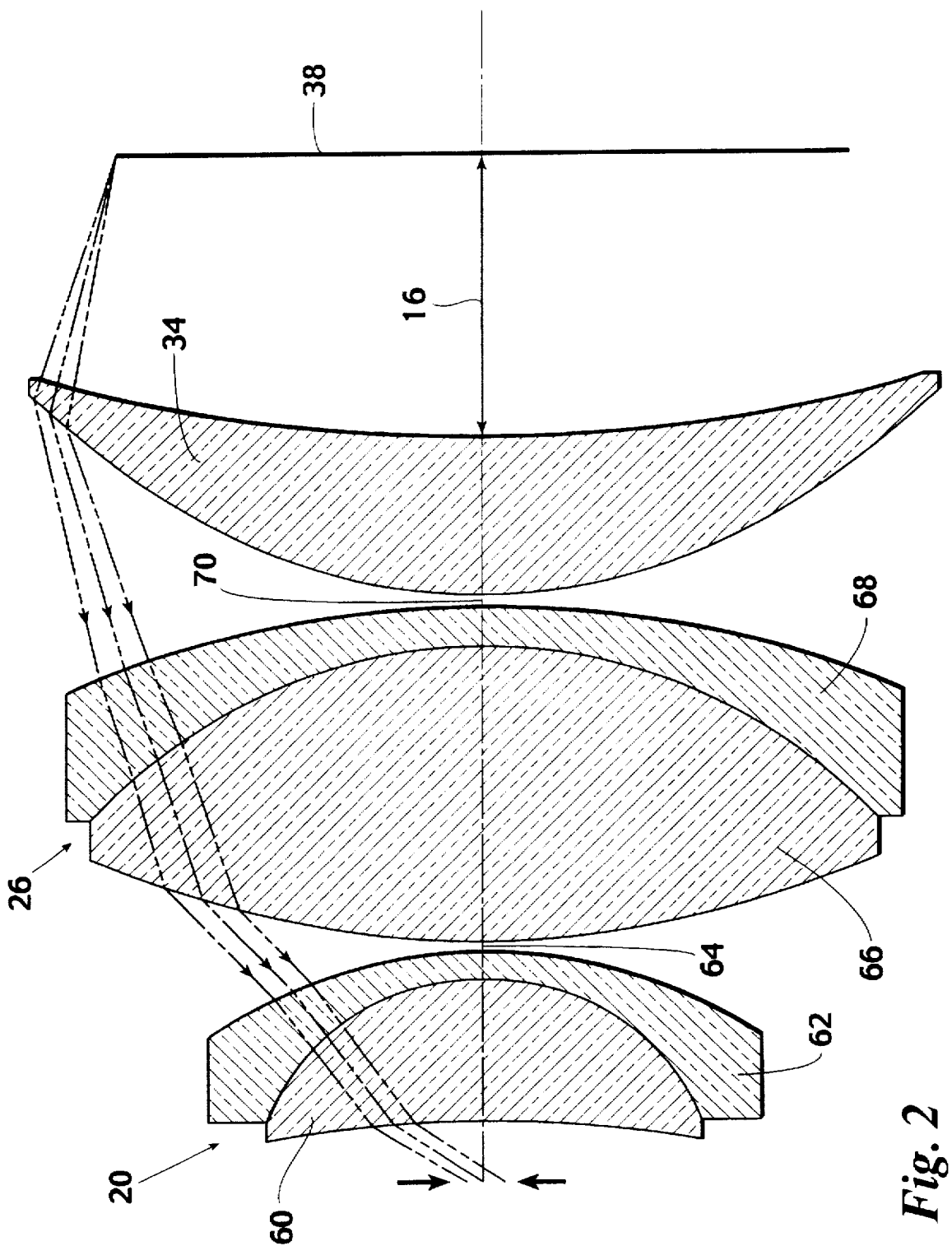
FIG. 2 is an elevational view of a preferred lens assembly.

FIG. 2 shows in more detail the preferred lens complex. The preferred lens assembly has a maximum diameter of 76 mm. It consists of a pair of doublet lenses 20, 26 and a singlet lens 34 placed in series and oriented transverse to the line of sight 16. As can be easily seen in FIG. 2, a required characteristic of the lens assembly is that it have the capability to provide an ultra wide field of view, projecting the image steeply toward the viewing aperture 14. Other lens assemblies constructed as is known in the art would suffice so long as they have the ability to sharply angle the image of the iris diaphragm 38 to the eye and are sized so as to be adaptable to a small hand-held device.

The lens complex shown in FIG. 2 is sufficient to provide a 60° half field of view. As indicated, the distance between the first surface of the lens complex and the pupil is approximately 5 mm. The first surface 60 of the initial doublet 20 has a radius of curvature of approximately −121 mm and a center thickness, measured along the line of sight 16, of approximately 13.44 mm. This component has an index of refraction of approximately 1.62 and a diameter of approximately 38 mm. The second surface 62 of the initial doublet 20 has a radius of curvature of approximately −20 mm and a center thickness of approximately 2.4 mm. Its index of refraction is about 1.72 and its diameter is also 38 mm. The space 64 between the first doublet 20 and the second doublet 26 is approximately 0.8 mm in length.

The first surface 66 of the second doublet 26 has a radius of curvature of approximately 85 mm and a center thickness of about 27 mm. Like the first surface 60 of the initial doublet 20, its index of refraction is 1.62; however its diameter is about 66 mm. The second surface 68 of the second doublet 26 has a radius of curvature of approximately −40 mm and a center thickness of about 2.4 mm. Similar to the second surface 62 of the initial doublet 20, its index of refraction is 1.72; however its diameter is approximately 66 mm. The space 70 between the second doublet 26 and the singlet lens 34 is approximately 0.8 mm in length.

The singlet lens 34 has a radius of curvature of approximately 48 mm and a center thickness of 13.44 mm. Its index of refraction is 1.62, and its diameter is 76 mm. There is approximately 25.6 mm between the rear surface of the single lens 34 and the iris diaphragm 38.

The effective focal length of the lens complex as a whole is about 35.65 mm. If discussed in the context of a microscope, whereby the lens would act as the eyepiece of the apparatus, the lens complex could be said to have an approximate magnification of 7×.

Figure 3:
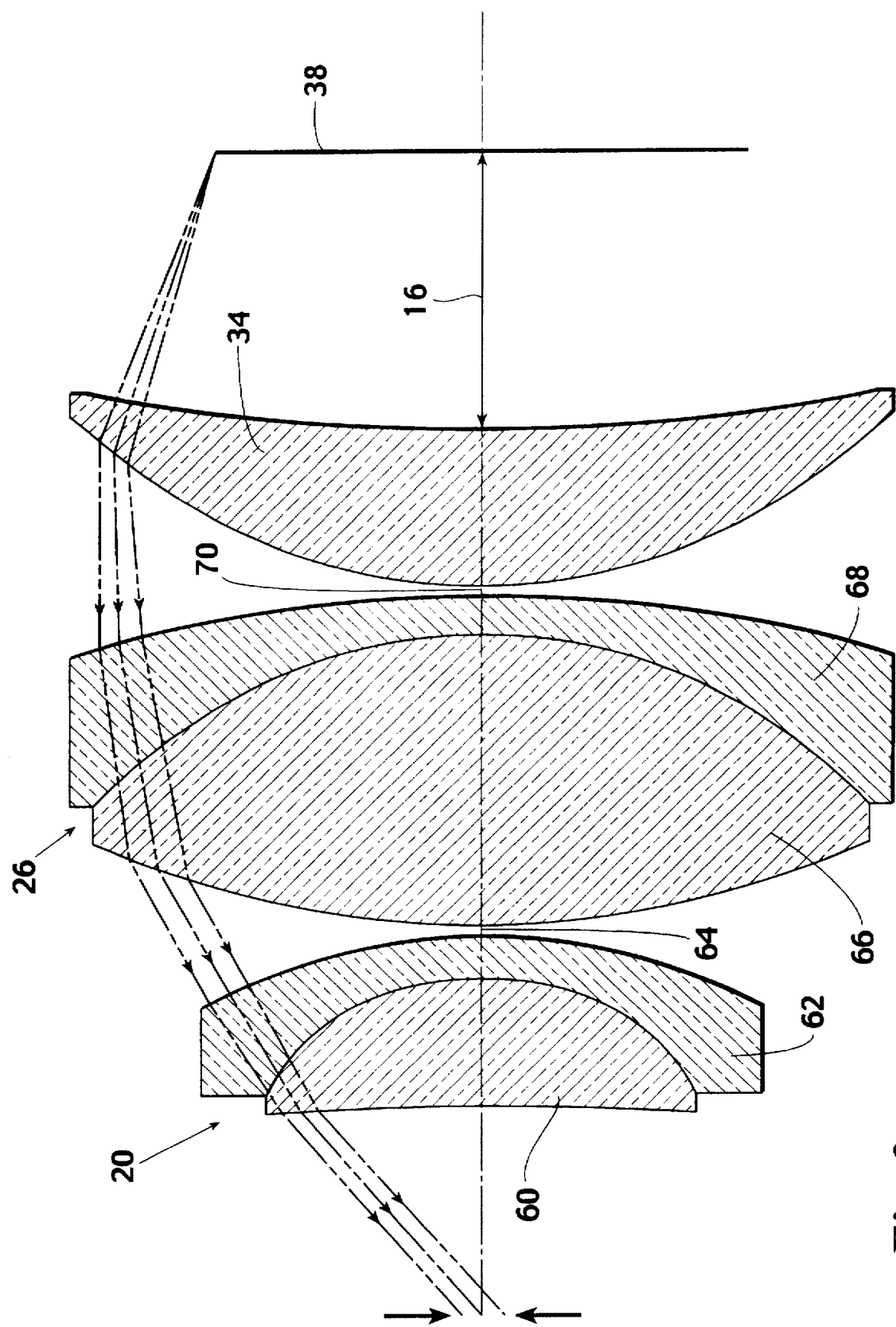
FIG. 3 is an elevational view of an alternate lens assembly.

FIG. 3 shows a lens complex similar to FIG. 2, however more distance has been provided between the viewing aperture 14 and the eye. A short standoff distance as shown in FIG. 2 might result in physical interference with a patient's nose or eyebrow. FIG. 3 shows an alternate embodiment which increases the standoff distance, but at the cost of compromising the field of view to some extent. In the FIG. 3 embodiment, the half field of view is 41°. The adjustable iris 38 has a maximum open aperture of 46 mm, but still possesses the capability of full closure. As is seen, the angular projection of the image is less severe than in the FIG. 2 embodiment.

While the invention has been described with a certain degree of particularity, it is manifest that many changes may be made in the method hereinabove described without departing from the spirit and scope of this disclosure. It is understood that the invention is not limited to the embodiments set forth herein for purposes of exemplification, but is to be limited only by the scope of the attached claim or claims, including the full range of equivalency to which each element thereof is entitled.

What is claimed is:

1. A field of view collimator for self-monitoring peripheral vision loss, comprising:

(a) a hand-held housing having a viewing aperture for placement adjacent to an eye;

(b) a lens means for projecting an image to said eye;

(c) an iris diaphragm positioned behind said lens means to provide said image in the form of a circular edge, the angular size of said image being adjustable by opening or closing said iris diaphragm to obtain a field of view reading;

(d) a diffuser positioned behind said iris diaphragm to provide an even back-illumination of said iris diaphragm; and (e) indicia means for indicating said field of view reading.

2. The field of view collimator according to claim 1, wherein the full field of view is 120 degrees.

3. The field of view collimator according to claim 1, wherein said iris diaphragm has a maximum open aperture of 60 mm and possesses the capability of full closure.

4. The field of view collimator according to claim 1, wherein said diffuser comprises ground glass.

5. The field of view collimator according to claim 1, further comprising a knurled ring for adjusting said iris diaphragm.

6. A method for self-monitoring peripheral vision loss, comprising:

(a) using a field of view collimator to obtain a field of view reading, said field of view collimator comprising a hand-held housing having a viewing aperture for placement adjacent to an eye, a lens means for projecting an image to said eye, an iris diaphragm positioned behind said lens means to provide said image in the form of a circular edge, the angular size of said image being adjustable by opening or closing said iris diaphragm to obtain said field of view reading, a diffuser positioned behind said iris diaphragm to provide an even back-illumination of said iris diaphragm, and indicia means for indicating said field of view reading;

(b) repeating step (a) on a regular basis;

(c) recording said field of view readings; and (d) reporting said field of view readings to a managing physician.

\* \* \* \* \*